(12) United States Patent
Bernardin et al.

(10) Patent No.: US 10,793,505 B2
(45) Date of Patent: Oct. 6, 2020

(54) UNIT AND PROCESS FOR PURIFICATION OF CRUDE METHYL METHACRYLATE

(71) Applicant: Arkema France, Colombes (FR)

(72) Inventors: Yves Bernardin, Thionville (FR); Romain Billon, Carrieres sur Seine (FR); Xavier Marcarian, Billere (FR); Florent Vallet, Ecully (FR)

(73) Assignee: Arkema France, Colombes (FR)

( * ) Notice: Subject to any disclaimer, the term of this patent is extended or adjusted under 35 U.S.C. 154(b) by 326 days.

(21) Appl. No.: 15/029,300

(22) PCT Filed: Oct. 17, 2014

(86) PCT No.: PCT/EP2014/072367
§ 371 (c)(1),
(2) Date: Apr. 14, 2016

(87) PCT Pub. No.: WO2015/055843
PCT Pub. Date: Apr. 23, 2015

(65) Prior Publication Data
US 2016/0251297 A1    Sep. 1, 2016

(30) Foreign Application Priority Data

Oct. 18, 2013 (FR) .................................. 13 60186

(51) Int. Cl.
*C07C 67/54* (2006.01)
*B01D 3/36* (2006.01)
(Continued)

(52) U.S. Cl.
CPC .............. *C07C 67/54* (2013.01); *B01D 3/143* (2013.01); *B01D 3/34* (2013.01); *B01D 3/36* (2013.01);
(Continued)

(58) Field of Classification Search
CPC ...... B01D 3/34; B01D 3/143; B01D 11/0446; B01D 3/36; C07C 51/44; C07C 51/50; C07C 67/54; C07C 67/58
See application file for complete search history.

(56) References Cited

U.S. PATENT DOCUMENTS 2,113,965 A * 4/1938 Roelfsema ............... B01D 3/40
203/58
3,085,153 A * 4/1963 Morgan ............... B01D 3/4238
203/3
(Continued)

FOREIGN PATENT DOCUMENTS

GB          1500474 A  *  2/1978  ............. C07C 67/54
JP      2001322968 A     11/2001
(Continued)

OTHER PUBLICATIONS

Rousseau, Ronald W.. (1987). Handbook of Separation Process Technology—5.7 Tray-Type Distillation Columns. (pp. 276-277). John Wiley & Sons. (Year: 1987).*
(Continued)

*Primary Examiner* — Jonathan Miller
*Assistant Examiner* — Gabriel E Gitman
(74) *Attorney, Agent, or Firm* — Thoms F. Roland

(57) ABSTRACT

The invention relates to a purification unit (200) which is able to separate crude MMA from light and heavy impurities in order to obtain high quality of MMA, suitable to produce optimal grade polymethylmethacrylate (PMMA). The unit (200) comprises two distillation columns (210, 250) in series, fed with mixture to be distilled in their median part, in order to separate each column in two upper (213, 253) and lower (212, 252) parts, the first distillation column (210) being fed with crude prewashed MMA, and the second distillation column (250) being fed with distilled liquid stream containing MMA, separated from light impurities, (Continued)

Figure 1:
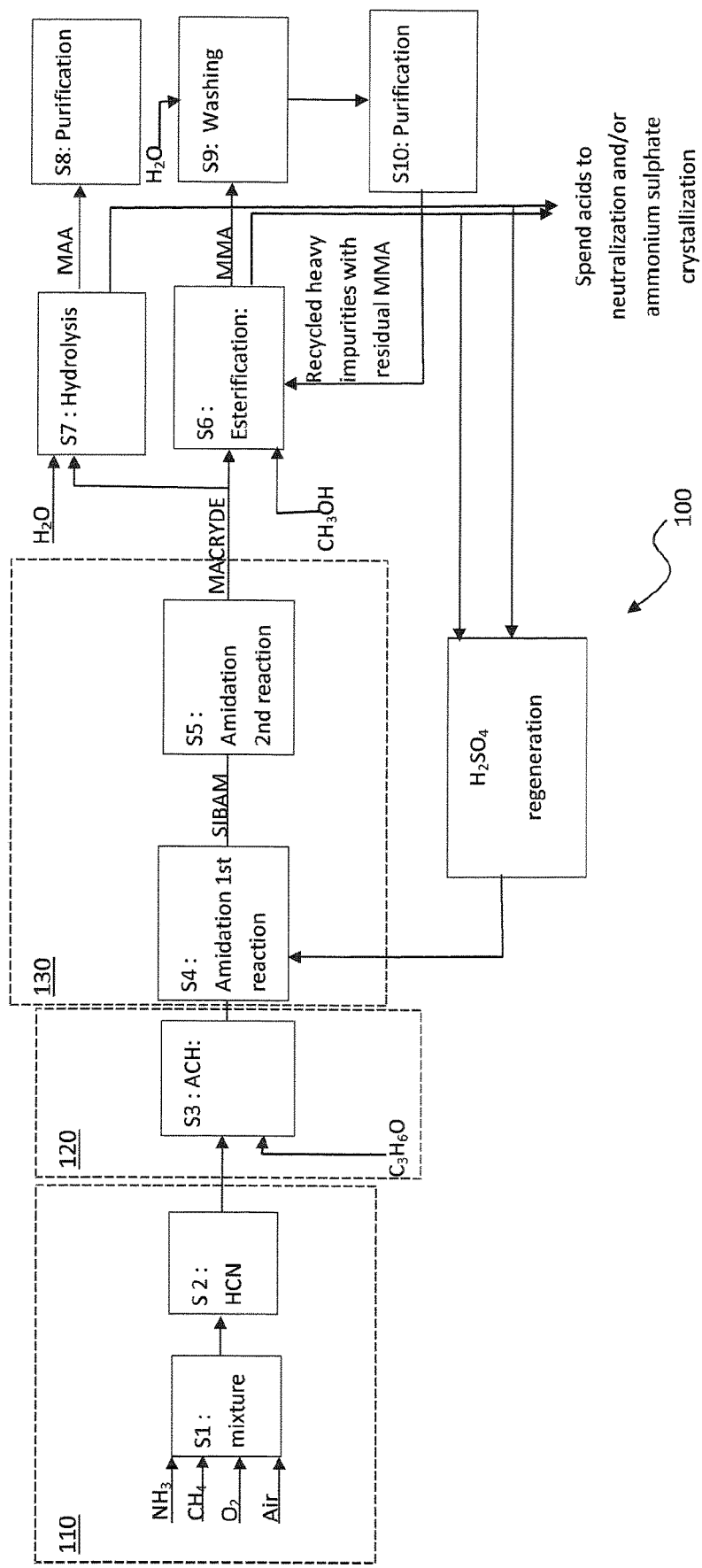

issued from bottom of first distillation column (210). The upper part (213) of first distillation column (210) is connected to a lateral extraction system (220), able to minimize MMA content in light impurities flowing upward said first column (210).

24 Claims, 2 Drawing Sheets

(51) Int. Cl.
    *B01D 3/14*     (2006.01)
    *C07C 67/58*     (2006.01)
    *B01D 3/34*     (2006.01)
    *B01D 11/04*     (2006.01)
    *C07C 51/44*     (2006.01)
    *C07C 51/50*     (2006.01)

(52) U.S. Cl.
    CPC .......... *B01D 11/0446* (2013.01); *C07C 51/44* (2013.01); *C07C 51/50* (2013.01); *C07C 67/58* (2013.01)

(56) References Cited

U.S. PATENT DOCUMENTS

| | | | | |
|---|---|---|---|---|
| 3,449,215 A * | 6/1969 | Lupfer | ................... | B01D 3/425 203/3 |
| 5,028,735 A * | 7/1991 | Segawa | ................... | C07C 29/88 560/218 |
| 5,092,983 A * | 3/1992 | Eppig | ................... | B01D 11/02 208/13 |
| 5,207,874 A | 5/1993 | Hess et al. | | |
| 5,435,892 A * | 7/1995 | Miyazaki | ................. | B01D 3/34 203/95 |
| 5,980,695 A * | 11/1999 | Cox | ......................... | B01D 3/42 202/166 |
| 2001/0030120 A1* | 10/2001 | Mitsumoto | ........... | B01D 3/225 203/99 |
| 2002/0192132 A1* | 12/2002 | Carlson, Jr. | .......... | B01D 1/0017 203/88 |
| 2003/0205451 A1* | 11/2003 | Briegel | .................. | B01D 3/146 203/1 |
| 2004/0222077 A1* | 11/2004 | Yada | ........................ | B01D 3/10 203/1 |
| 2004/0267050 A1* | 12/2004 | DeCourcy | ............... | C07C 51/44 562/600 |
| 2005/0059838 A1 | 3/2005 | Yada et al. | | |
| 2005/0189296 A1* | 9/2005 | Yada | .................. | B01D 11/0426 210/634 |
| 2006/0249365 A1* | 11/2006 | Yada | ........................ | B01D 3/14 202/152 |
| 2008/0035466 A1* | 2/2008 | John O. | .................... | B01D 3/16 203/4 |
| 2008/0194875 A1 | 8/2008 | Ackermann et al. | | |
| 2010/0029881 A1* | 2/2010 | Gropp | ................... | C07C 231/06 526/319 |
| 2014/0154758 A1 | 6/2014 | Dubois et al. | | |

FOREIGN PATENT DOCUMENTS

| | | |
|---|---|---|
| JP | 2007045803 A | 2/2007 |
| JP | 2009062289 A | 3/2009 |
| WO | WO 2013146609 | 10/2013 |

OTHER PUBLICATIONS

Caballero, Jose and Grossman, Ignacio. (2014). Distillation: Fundamentals and Principles—Optimization Background. Chapter 11: Optimization of Distillation Processes. Editors: Górak, Andrzej; Sorensen, Eva. Elsevier. (Year: 2014).*

* cited by examiner

UNIT AND PROCESS FOR PURIFICATION OF CRUDE METHYL METHACRYLATE

This application claims benefit, under U.S.C. § 119 or § 365 of PCT Application Number PCT/EP2014/072367, filed Oct. 17, 2014, and French Patent Application Number FR13.60186, filed Oct. 18, 2013, these documents being incorporated herein by reference.

FIELD OF THE INVENTION

The present invention relates to a continuous industrial process for the production of methyl methacrylate (MMA). It relates more particularly to a step of such industrial process, which concerns the purification of methyl methacrylate. The invention relates more precisely to a purification unit which is able to separate crude MMA from light and heavy impurities in order to obtain high quality of MMA, suitable to produce optimal grade polymethylmethacrylate (PMMA).

STATE OF THE ART

A number of commercial processes are used to prepare monomer selected from methacrylic acid (also called "MAA" in the following description) and/or methyl methacrylate (also called "MMA" in the following description). One of these processes consists in preparing such monomer from acetone cyanohydrin (ACH). Such a process is for example described in US patent application US2010/0069662. In this process, acetone cyanohydrin ACH is hydrolysed by sulphuric acid to produce an hydrolysis mixture, which is then thermally converted, into a mixture comprising 2-methacrylamide (MAM). MAM can then be used to produce either MMA, by reaction of esterification with methanol, or MAA by reaction of hydrolysis with water.

Other processes consist in preparing MMA by "C4 route" for example, i.e. from isobutene or Ter-butanol, or by "C2 route" from ethylene, or by new routes such as "alpha process" from ethylene with carbon monoxide and methanol.

Methyl methacrylate MMA is mostly used to produce polymer such as polymethylmethacrylate (also called "PMMA") which has multiple applications like for example automotive, transport, aerospace, photovoltaic, informatics, telecommunications, wind energy, or building construction. MMA can also be used to produce other methacrylates by means of trans-esterification.

The MMA market is extremely cost sensitive. A slight improvement in process yield can result in a significant market advantage.

Particularly, the MMA has to be of high purity, typically higher than 99.8%, in order to be able to produce high quality methacrylates or high quality polymethylmethacrylates PMMA or optical grade PMMA.

The known methods for purifying MMA are complex and require a lot of steps. They use at least three columns, the two first being distillation columns for separating MMA from light and heavy impurities and the third being either another distillation column or an absorption column like a molecular sieve column for example, for removing any other residual impurities. Such purification of MMA is for example described in patent application US2010/0029881.

The document US2008/194875 discloses a method for producing alkyl (meth)acrylates. The intention is to provide a process with a high selectivity and a small amount of by-products. The product is purified by distillation and product recovered on the top of the column.

The document FR2656305 discloses a purification process for glycidyle (meth)acrylate. The process comprises several columns, where all columns have only extraction lines at the top or the bottom of each respective column.

The document WO2013/256609 discloses a method for purifying acetonitrile. The process comprises two separations columns. The two columns have only line lines only at the top and the bottom of the each column.

The document JP2009-62289 discloses a method for producing acrylic acid and (meth)acrylic acid ester. During purification the process uses an online analysis for adjusting the process parameters.

The document US2005/0059838 discloses a process for producing (meth)acrylic acid compound. The process uses several separation columns or purification columns. All the discharge lines are either at the top or at the bottom of the respective columns.

The document JP2007-45803 discloses a method for obtaining purified methyl methacrylate. The purification is especially in point of view to reduce the content of byproducts/impurities that influence the colour. All the discharge lines for the products are either at the top or at the bottom of the respective columns.

The document JP2001-322968 discloses a method for purifying methacrylic acid esters. The method of purification implies several columns. All the discharge lines for the products are either at the top or at the bottom of the respective columns.

However, the applicant has discovered that the known methods could be further improved in order to simplify the purification process by reducing the number of steps, while further increasing the purity. Moreover, the applicant has also discovered that yield of purification could also be improved. In fact, with the known methods of purification, there are losses of MMA, which is driven with the rejected impurities. Moreover, it is also important to control the purification process so as to avoid polymerization of MMA.

Therefore, there is a need for improving the purification process of MMA, by simplifying the steps involved, while allowing the obtaining of an ultra-high purity of MMA, and an increase of the yield by reducing the losses of MMA and avoiding the MMA polymerization.

TECHNICAL PROBLEM

Present invention aims to avoid at least one of the inconveniences of the state of the art. More particularly, the invention aims to propose a simpler purification unit, which allows increasing purity of obtained MMA, increasing the yield of the purification and controlling the MMA polymerization phenomenon. The invention aims also to reduce the number of steps of the purification process. The invention aims also to a purification process with a reduced number of distillation columns.

BRIEF DESCRIPTION

For this purpose, the invention relates to a methyl methacrylate purification unit able to separate methyl methacrylate (MMA) from light and heavy impurities, said unit being characterized in that it comprises two distillation columns (210, 250) in series, fed with the mixture to be distilled in their median parts, in order to separate each column in two upper and lower parts, the first distillation column being fed with crude prewashed methyl methacrylate (MMA), and the second distillation column being fed with distilled liquid stream containing methyl methacrylate (MMA), separated from light impurities, issued from bottom of first distillation column, and the upper part of first distillation column is connected to a lateral extraction system, able to minimize methyl methacrylate (MMA) content in a gas phase of light impurities flowing upward said first column. By minimize is meant that there are at least 5% less of methyl methacrylate in the gas phase of light impurities flowing upward said first column in comparison to a purification unit without said lateral extraction system connected at the upper part of first distillation column.

The invention relates also to a methyl methacrylate purification unit able to separate methyl methacrylate (MMA) from light and heavy impurities, said unit being characterized in that it comprises two distillation columns in series, fed with mixture to be distilled in their median part, in order to separate each column in two upper and lower parts, the first distillation column being fed with crude prewashed methyl methacrylate (MMA), and the second distillation column being fed with distilled liquid stream containing methyl methacrylate (MMA), separated from light impurities, issued from bottom of first distillation column, and the upper part of first distillation column is connected to a lateral extraction system.

Thus the division of each distillation column in two parts improves the separation between MMA and impurities, so that it contributes to the obtaining a high degree of purity of the obtained distilled MMA. The purity of the obtained MMA is higher than 99.90 wt %, and more preferably higher than 99.96 wt %. The lateral extraction system allows avoiding losses of MMA, by preventing the discharge of an azeotropic mixture of MMA and water with light impurities, so that the yield of purification of MMA is increased. The MMA losses during the process are less than 0.5%, and more preferably less than 0.25%.

According to another particularity, the lateral extraction system comprises a feeding pipe for adding water to the light impurities containing a MMA-water azeotropic mixture extracted from an extraction liquid outlet located in the upper part of first distillation column, a cooling device for cooling the obtained mixture, at a temperature between 20° C. and 34° C., and a settler for recovering the liquid phase and for obtaining a phase separation between an aqueous phase containing water and methanol, and an organic phase containing methyl methacrylate (MMA), said settler being connected to an inlet of the first distillation column located below said extraction liquid outlet, in order to re-inject organic phase containing methyl methacrylate (MMA) inside upper part of said first distillation column.

The settler further comprises an outlet at its bottom through which the aqueous phase flows to be recycled towards a washing unit of crude methyl methacrylate MMA.

According to another particularity, the bottom of each distillation column is connected to a reboiler system able to re-inject a vaporized part of distilled liquid stream into the respective lower part of each column, while the liquid part of said stream flows towards a pump.

According to another particularity, top of each column is respectively connected to a condenser system for liquefying gas phase, and a reflux drum which recovers the obtained liquid phase and a pump which recycles part of said obtained liquid phase into the respective upper part of said column.

According to another particularity, each upper and lower part of each distillation column comprises between 4 and 30 trays or plates.

According to another aspect, the invention relates to a process for purifying crude methyl methacrylate (MMA), said crude MMA being prewashed with water before the purification, said process being characterized in that it comprises following steps:
  introduce pre-washed crude methyl methacrylate (MMA) in a median part of a first distillation column, in order to separate said first column into a lower and an upper part, at least 90% of introduced MMA and heavy impurities flowing downward of said first column with liquid phase, and at least 98% of introduced light impurities flowing upward with gas phase, liquid phase being further laterally extracted at an extraction liquid outlet located in the upper part of said first distillation column, in order to be cooled and washed with water and to obtain a phase separation between an aqueous phase containing water and methanol, and an organic phase containing MMA which is recycled into said upper part of said first distillation column, below said extraction liquid outlet,
  introduce liquid phase issued from bottom of first distillation column into a median part of a second distillation column in order to separate said second column into a lower and an upper part, at least 98% of introduced heavy impurities flowing downward of said second distillation column with liquid phase, while at least 90% of introduced purified MMA flows upward with gas phase.

INTRODUCTION OF THE FIGURES

Figure 2:
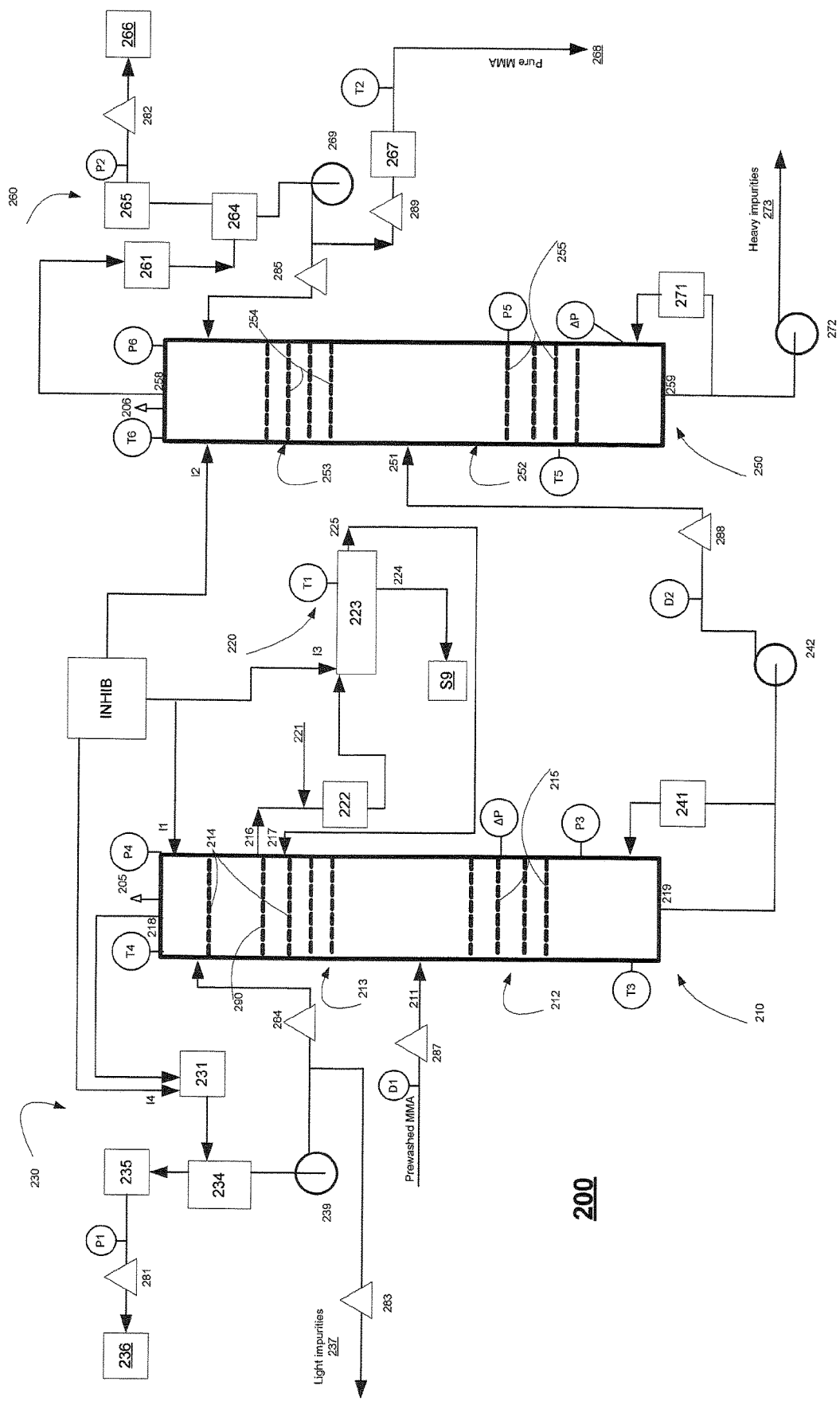

Other features and advantages of the invention will become apparent upon reading the following description given by way of illustrative and non-limiting examples, with reference to the accompanying Figures in which:
  FIG. 1 represents a simplified schematic bloc diagram of a plant for preparing methacrylic acid and/or methyl methacrylate,
  FIG. 2 represents a simplified scheme of a purification unit according to the invention.

SPECIFICATION

The distillation columns used in the purification unit described in the specification have a substantially cylindrical shape, the height of the cylinder defining a vertical axis of the column, perpendicular to the ground.

The terms "top", "upper" or "above" and "down", "bottom", or "lower" are used to define a portion of a column with respect to the vertical axis of said column. The pairs "top" and "upper" as well as "bottom" and "lower" define different parts of the column. In the present invention the "top" is not considered as part of a "upper" part of the column and the "bottom" is not considered as part of the "lower" part of the column. A column comprises an upper part and above of the upper part is the top. Likewise a column comprises a lowerpart and still below the lower part is the bottom of the column.

The terms "upstream" and "downstream" are defined relative to the direction of a fluid flowing through the devices of a plant for the production of a final product such as methyl methacrylate (MMA) or methacrylic acid (MAA).

The terms "light impurities", or "low boiling point impurities" mean impurities that have a lower boiling point than the MMA boiling point. The terms "heavy impurities" or "high boiling point impurities" mean impurities that have a higher boiling point than the MMA boiling point.

The process for production of crude MMA described just below is a well-known process using acetone cyanohydrin. However, it must be noticed that the purification unit and process of the present invention is used to purify crude MMA whatever is the process route used to produce MMA.

Concerning the Synthesis of Monomer Selected from Methacrylic Acid and/or Its Esters FIG. 1 shows a simplified schematic bloc diagram of a plant for the production of methacrylic acid and/or its esters from acetone and hydrogen cyanide HCN prepared by the Andrussow process. The Andrussow process is for example described in the document U.S. Pat. No. 1,934,838.

Such monomers can be further used to produce for example polymethylmethacrylate (PMMA) that is a polymer widely used in a lot of applications like for example automotive, transport, aerospace, photovoltaic, informatics, telecommunications, wind energy, or building construction.

Preparation of Hydrogen Cyanide HCN

First of all (steps S1 and S2) HCN is produced in a first unit 110, from a mixture of methane-containing gas, ammonia and air eventually enriched with oxygen. A mixture of reactant gases is prepared (step S1), and introduced (step S2) into an. Andrussow type reactor comprising catalyst gauzes based on platinum/rhodium gauzes. Mixture of gases passes over the catalyst gauzes and reacts at a temperature comprised between 750° C. and 1250° C. and preferably between 1000° C. and 1200° C., to form HCN. The oxygen-enriched air enables an increase in productivity and reduces the methane consumption. The HCN produced is quickly cooled and treated so as to avoid polymerization of HCN. For that, ammonia which has not reacted is absorbed by reaction with sulfuric acid, and the HCN is absorbed and stabilized in an absorption column, and then distilled in a distillation column to reach a purity of 99.5% wt.

Preparation of Acetone Cyanohydrin ACH

The thus synthesized HCN is then mixed with acetone ($C_3H_6O$), in a unit 120 designed for the production of acetone cyanohydrin ACH (step S3). The crude acetone cyanohydrin obtained is then purified by distillation.

Amidification of Acetone Cyanohydrin

A third unit 130 of the plant is provided for amidification of acetone cyanohydrin. Such amidification of ACH requires two steps S4 and S5 for producing 2-methacrylamide (also called "MACRYDE" in the following description).

First, in step S4, sulphuric acid ($H_2SO_4$) is added in excess in comparison with acetone cyanohydrin ACH. For example the molar ratio of $H_2SO_4$/ACH is comprised between 1.2 and 2, preferably between 1.25 and 1.8, and more preferably between 1.3 and 1.6.

This first reaction occurring is an hydrolysis reaction of ACH by sulphuric acid, which gives an intermediate salt, called the SIBAM (for α-sulfatoisobutyramide). This reaction is the following:

$$(CH_3)_2COHCN+H_2SO_4 \rightarrow (CH_3)_2COSO_3HCONH_2 \quad (1)$$

Acetone cyanohydrin (ACH) α-sulfatoisobutyramide (SIBAM)

This reaction is fast and exothermic. The temperature is around 90° C.-95° C. and the pressure is close to the atmospheric pressure.

The second reaction (step S5) is a slow and endothermic reaction. It occurs at atmospheric pressure and a temperature range between 110° C. and 165° C., preferably between 125° C. and 150° C. and more preferably between 130° C. and 145° C. This reaction is a cooking reaction which lasts between 3 and 16 minutes. This reaction is the following:

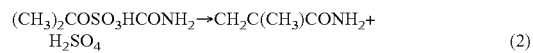

α-sulfatoisobutyramide (SIBAM) 2-methacrylamide (MACRYDE)

During the synthesis reactions there are many other by-products. The main side reaction is described below.

The first hydrolysis reaction of ACH by a small quantity of water can create a significant quantity of HIBAM (α-hydroxyisobutyramide). Such a reaction is very fast. It is the following:

$$(CH_3)_2COHCN+H_2O \rightarrow (CH_3)_2COHCONH_2 \quad (3)$$

Acetone cyanohydrin (ACH) α-hydroxyisobutyramide (HIBAM)

In the second step S5, HIBAM can also create MACRYDE, but this reaction is very slow. So there is a large quantity of unconverted HIBAM at the end of amidification step S5. The reaction is the following:

$$(CH_3)_2COHCONH_2 \rightarrow CH_2C(CH_3)CONH_2+H_2O \quad (4)$$

α-hydroxyisobutyramide (HIBAM) methacrylamide (MACRYDE)

The hydrolysis of HIBAM may create HIBA (α-hydroxyisobutyricacid)

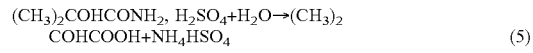

α-hydroxyisobutyramide (HIBAM) α-hydroxyisobutyricacid (HIBA)+ammoniumbisulfate

At the same time, a significant amount of methacrylic acid MAA is produced by the hydrolysis of SIBAM by water. This reaction is the following:

$$(CH_3)_2COSO_3HCONH_2+H_2O \rightarrow CH_2C(CH_3)COOH+NH_4HSO_4 \quad (6)$$

α-sulfatoisobutyramide (SIBAM) methacrylic acid (MAA)+ammoniumbisulfate

The mixture of MACRYDE and MAA obtained after amidification is then either hydrolyzed (step S7), by adding water to the MACRYDE mixture, or esterified (step S6), by adding methanol to the MACRYDE mixture.

Esterification

The components obtained after amidification, namely the methacrylamide and the methacrylic acid, are esterified, so as to obtain methyl methacrylate MMA. The esterification reaction (step S6) is made by mixing said components with methanol ($CH_3OH$).

The main reactions are these two below:

$$CH_2C(CH_3)CONH_2, H_2SO_4+CH_3OH \rightarrow CH_2C(CH_3)COOCH_3+NH_4HSO_4 \quad (7)$$

methacrylamide (MACRYDE)+methanol methyl methacrylate (MMA)+ammoniumbisulfate $$CH_2C(CH_3)COOH+CH_3OH \rightarrow CH_2C(CH_3)COOCH_3+H_2O \quad (8)$$

methacrylic acid (MAA)+methanol methyl methacrylate (MMA)

Hydrolysis

The components obtained after amidification can also be hydrolysed by mixing them with water (step S7). Such hydrolysis reaction allows to obtain methacrylic acid according to the following reaction:

$$CH_2C(CH_3)CONH_2, H_2SO_4+H_2O \rightarrow CH_2C(CH_3)COOH+NH_4HSO_4 \quad (9)$$

methacrylamide (MACRYDE) methacylic acid (MAA)+ammoniumbisulfate

Purification of Crude MMA or MAA Obtained

Either the crude methyl methacrylate MMA obtained after esterification (S6) or the crude methacrylic acid MAA obtained after hydrolysis (S7) is then purified (respective steps S10 and S8), in order to remove residual compounds.

Before purification, crude MMA is advantageously washed by adding an excess of water. Crude MMA, which is recovered from esterification unit, contains mainly MMA (generally between 50% mol and 80% mol), water (generally between 10% mol and 20% mol) and methanol (generally between 10% mol and 20% mol). It contains also heavy and light impurities. Amongst the heavy impurities, there are products like for example methyl alpha hydroxyisobutyrate, ethyl methacrylate, methacrylic acid, methyl pivalate and other heavy impurities. Amongst the light impurities, there are products like for example methyl isobutyrate, methyl propionate, methyl acrylate, acetone and other light impurities.

Crude MMA obtained after esterification of MACRYDE is washed in an extraction unit (Step S9), to remove water and methanol from MMA. Indeed, MMA forms azeotropic mixtures with water and methanol, and it is impossible to separate these components by distillation. Therefore, crude MMA is washed with an excess of demineralized water in order to induce a phase separation, thereby obtaining an aqueous phase containing water and methanol, which is recycled to the esterification step (S6), and an organic phase containing MMA, less water and methanol and other heavy and light impurities.

Concerning the Purification of Prewashed Crude MMA

FIG. 2 shows a simplified scheme of a purification unit 200 according to the invention. This unit 200 comprises only two distillation columns 210, 250 in series. Each distillation column 210, 250 is fed with mixture to be distilled at an input 211, 251 located in a median part, so that each column is divided in two parts, respectively a lower part 212, 252 and an upper part 213, 253.

The prewashed crude MMA (from step S9 of FIG. 1) is introduced in an inlet 211 located in the median part of the first distillation column 210. At least 90% of introduced MMA with heavy impurities flows towards the bottom of the column with the liquid phase, while at least 98% of introduced light impurities flow upward with gas phase.

In order to avoid MMA polymerization, each distillation column 210, 250 is connected to a dedicated vacuum system, respectively referenced 236, 266. Such a vacuum system may be made of any known type of vacuum pump, such as for example a liquid ring vacuum pump or a dry compressor system or any other equivalent equipment, etc. The vacuum system is connected downstream a condensers system 230, 260, and allows sucking incondensable vents. The pressure at the bottom of each column is advantageously comprised between 66.66 mbar and 666.6 mbar, and preferably between 266.65 mbar and 586.62 mbar. More preferably, the pressure inside the second distillation column 250 is lower than the pressure inside the first distillation column 210. The vacuum is regulated by a pressure measurement, by means of a pressure sensor P1, P2, at the suction part of each vacuum system 236, 266 and with a control valve 281, 2.82 for partial gas recycling in the vacuum pump.

Such a depression inside both distillation columns 210, 250 allows decreasing the temperature inside the columns and thus, preventing MMA polymerization. Thus, the temperature inside both columns is advantageously lower than 90° C., and preferably lower than 85° C.

There are small residual quantities of water and methanol in the prewashed crude MMA, so that MMA forms a first azeotropic mixture with water and a second azeotropic mixture with methanol. Components of such azeotropic mixtures cannot be separated by distillation, so that they are usually rejected with light impurities. Consequently, due to the content of azeotropic mixture in the light impurities flowing upward the column with the gas phase, large amounts of MMA are usually rejected and lost.

In order to avoid or reduce these large losses of MMA, a lateral extraction of the light impurities containing the MMA-water azeotropic mixture, is made in the upper part of the first column 210. For that, an extraction liquid outlet 216, located in the upper part 213 of the first distillation column 210, and more precisely at a tray 290 of the upper part of first column, is connected to a lateral extraction system 220, which enables another washing of the stream of light impurities containing the MMA-water azeotropic mixture, with cold demineralized water. The stream is extracted from the extraction liquid outlet 216 by gravity towards the lateral extraction system 220, The lateral extraction system 220 comprises a feeding pipe 221 for adding demineralized water into the extracted stream, a cooling device 222 for cooling the obtained mixture, at a temperature between 20 and 34° C., and a settler 223 for recovering the liquid phase. The liquid phase comprises an excess of water, a phase separation appears in the settler. The settler 223 comprises a lower layer of aqueous solution comprising water and methanol. This aqueous solution flows through an outlet 224 at the bottom of the settler and can be recycled towards the washing unit (S9 of FIG. 1) for example for the washing step of crude MMA obtained after esterification step (S6). The settler 223 further comprises an upper layer of an organic phase comprising MMA and other light impurities. The settler 223 comprises another outlet 225 at the upper part of the settler, connected to an inlet 217 of the first column located just below the extraction liquid outlet 216, in order to recycle the organic phase containing MMA into the upper part 213 of the first distillation column 210. Thus, the recovered MMA flows downward and the light impurities flow upward. The temperature of the settler is supervised, by a temperature sensor T1, in order to control the efficiency of the cooling device 222. Moreover, the lateral extraction flowrate is preferably adjusted according to the water content in the feed stream of prewashed crude MMA, so as to reach a content of water, in the bottom of the first distillation column 210, preferably lower than 100 ppm.

The extraction liquid outlet 216 feeding the lateral extraction system 220 is located in the upper part 213 of the first distillation column 210, but not at the top 218. The location of the extraction liquid outlet at the trays in the upper part 213 of the first distillation column 210 is important for extracting a liquid simply by gravity. This avoids a condenser or other means if the extraction would take place in the gas phase.

Such a lateral extraction system 220 prevents or reduces losses of MMA that would normally be rejected with light impurities due to the fact that MMA forms azeotropic mixture with water and cannot be separated from water by simple distillation. Thus, the lateral extraction system enables to increase the yield of the purification.

At least 5%, preferably at least 10% of methyl methacrylate that would have been lost in the gas phase with the light impurities flowing upward said first column are gained in the present invention, in comparison to a purification unit without said lateral extraction system connected at the upper part of first distillation column.

Then, the light organic impurities stream flows from the top of the first distillation column 210 towards a condenser system 230 for liquefying part of the gas phase. The obtained liquid is recovered in a reflux drum 234. The condensers system 230 comprises at least one condenser 231, preferably two condensers, and more preferably three condensers. In a preferred embodiment, a first condenser 231, placed just downstream the outlet 218 of the top of the first column 210, is fed with cooling water, whose temperature is comprised between 20° C. and 34° C., and a second condenser (not shown) placed downstream the first, is fed with chilling water, whose temperature is comprised between 4° C. and 15° C. Another condenser 235, also called "trap condenser", fed with liquid brine or glycol water, whose temperature is comprised between −20° C. and −5° C., allows trapping ultra-light impurities which are very volatile. Finally, incondensable vents are then sucked up to the vacuum system 236.

After the reflux drum 234, the light impurities organic liquid phase is pumped with a pump 239 and partially recycled to the top of the upper part 213 of the first distillation column 210. Such reflux allows advantageously to recover MMA from azeotropic mixture of MMA and methanol and thus to reduce MMA losses. The reflux rate is adjusted to reduce MMA losses in top of column. The reflux rate is the ratio between flowrate recycled to the column and the flowrate sent outside the distillation system. This reflux rate may vary between 10 and 50. The reflux rate is also adjusted to control the temperature at the top of the column, to avoid an increase of temperature, which can promote a MMA polymerization. The reflux rate is adjusted by means of a control valve 284. The excess of light impurities organic liquid phase may be pumped to a waste storage or valorised, like for example burnt into a boiler to produce steam (referenced 237 on FIG. 2). A level control of the reflux drum 234 is done by a control valve 283 on the stream of light impurities intended to be stored or valorized.

The condenser system 230 with the recycle of part of light impurities organic phase allows to minimize MMA content in light impurities and to reduce the MMA losses. Thus, this system also allows increasing the yield of purification.

At the bottom of this first distillation column 210, there is a reboiler 241. Such a reboiler can be of different known type, like for example a thermosyphon reboiler or of a kettle type boiler. The reboiler 241 is fed with steam, which provides heat used to boil the liquid phase exiting the bottom outlet 219 of the first distillation column 210 and generates vapors, which are then returned to the lower part 212 of the column 210 to drive the distillation separation. The heat supplied to the column by the reboiler at the bottom of the column is removed by the condensers system 230 connected to the top of the column. The bottom temperature of the first column 210 is carefully monitored by means of a temperature sensor T3 and controlled by adjusting the steam flowrate in the reboiler. Thus, this reboiler 241 allows minimizing light impurities content in distilled liquid phase comprising MMA and heavy impurities. The obtained distilled liquid phase comprises less than 200 ppm of water, and preferably less than 100 ppm, only few 10 ppm of methanol and/or acetone, and less than 500 ppm of total light impurities, and more preferably less than 400 ppm.

Distilled liquid phase, comprising MMA and heavy impurities, which exits from the bottom outlet 219 of first distillation column 210, is then pumped with a pump 242 towards the second distillation column 250.

Liquid MMA-containing phase is introduced laterally in an inlet 251 located in the median part of second distillation column 250, so that this column is also divided in two parts, a lower part 252 and an upper part 253.

At least 98% of introduced heavy impurities and a small quantity of MMA flow down with liquid phase, whereas at least 90% of introduced purified MMA flows upward with gas phase.

Pure MMA is then condensed by means of a condensers system 260 connected to an outlet 258 located on the top of the column.

As for the first distillation column, the condenser system 260 comprises at least one condenser 261, preferably two condensers, and more preferably three condensers. In a preferred embodiment, a first condenser 261, placed downstream the outlet 258 on top of the second distillation column 250, is fed with cooling water, whose temperature is comprised between 20° C. and 34° C., and a second condenser (not shown) placed downstream the first, is fed with chilling water, whose temperature is comprised between 4° C. and 15° C. A third condenser 265, also called "trap condenser" fed with liquid brine or glycol water, whose temperature is comprised between −20° C. and −5° C., allows trapping any possible residual ultra-light impurities, which are very volatile. Incondensable vents are then sucked up to the vacuum system 266. The obtained liquid is recovered in a reflux drum 264.

After the reflux drum 264, the pure MMA liquid phase is pumped with a pump 269 and partially recycled to the top of the upper part 253 of the second distillation column 250, in order to minimize heavy impurities content in pure MMA distillate. The reflux rate is adjusted by means of a control valve 285.

Obtained pure MMA is quickly chilled until 0° C., by means of a heat exchanger 267, which is fed with liquid brine or glycol water at a temperature comprised between −20° C. and −5° C. Such a chilling allows avoiding polymerization of the obtained pure MMA. The pure MMA has to be stored at 0° C., so as to avoid polymerization. Therefore, the temperature has to be controlled precisely, by means of at least one temperature sensor T2 which is connected to an alarm. A level control of the reflux drum 264 is done by a control valve 289 on the stream of obtained pure MMA to be stored. The storage of the obtained pure MMA is referenced 268 on FIG. 2.

In the bottom of the second distillation column 250 there is a reboiler 271 of the type of thermosyphon reboiler or of a kettle boiler. The reboiler is fed with steam, which provides heat used to boil the liquid phase exiting the bottom outlet 259 of the second distillation column 250 and generates vapors, which are returned to the lower part 252 of the column to drive the distillation separation. The heat supplied to the column by the reboiler at the bottom of the column is removed by the condenser system 260 connected at the top of the column. Thus this reboiler allows minimizing MMA content in heavy impurities liquid phase.

Distilled liquid phase comprising the heavy impurities is then pumped with a pump 272 and either stored or valorised by burning them into a boiler for example to produce steam. Another preferred solution consists in pumping the distilled liquid phase comprising heavy impurities towards esterification unit (step S6 in FIG. 1). Indeed, the distilled liquid phase comprising heavy impurities, which exits from the bottom outlet 259 of second distillation column 250 may contain up to 40 wt % of MMA. Therefore, in order to avoid MMA losses, heavy impurities with remaining MMA are preferably recycled towards esterification unit of the plant (referenced 273 on FIG. 2). Thus, MMA is then recovered with crude MMA whereas heavy impurities flow with spent acids.

The bottom temperature of the second column 250 is carefully monitored by means of a temperature sensor T5 and controlled by adjusting the steam flowrate in the reboiler. Thus, the MMA content in bottom distilled liquid phase is minimized.

Both vacuum systems 236, 266 enable to decrease pressure and temperature inside the columns for preventing MMA polymerization. However, although the temperature is lower than 90° C., it may appear not sufficient to prevent polymerization. That is why a polymerization inhibitor, able to prevent MMA polymerization, is preferably introduced in the distillation columns during the purification of MMA. For that, the inhibitor, referenced INHIB on FIG. 2, is preferably introduced at the top of each column (see respective inlets I1 and I2 on FIG. 2).

Such inhibitor can be chosen amongst: hydroquinone; 4-alcoxyphenol; hydroquinone monobenzylether; 1.2-dihydroxybenzene, 2-methoxyphenol; 2,5-dichlorohydroquinone; 2,5-di-ter-butylhydroquinone, 2-acethylhydroquinone; hydroquinone monobenzoate; 1,4-dimercaptobenzene, 1,2-dimercaptobenzene; 2,3,5-trimethylhydroquinone; 4-aminophenol, 2-aminophenol; 2-N,N-dimethylaminophenol; 2-mercaptophenol; 4-mercaptophenol; catechol; monobutylether; 4-ethylaminophenol; 2,3-dihydroxyaminophenone; pyrogallol; 1,2-dimethylether; 2-methylthiophenol; t-butyl catechol; di-ter-butylnitroxide; di-ter-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-ethanoyloxy-2,2,6,6-tetramethyl-piperidinyloxy; 2,2,5,5-tetramethyl-pyrrolidinyloxy; 3-amino-2,2,5,5-tetramethyl-pyrrolidinyloxy 2,2,5,5-tetramethyl-1-oxa-3-azacyclopentyl-3-oxy; 2,2,5,5-tetramethyl-3-pirrolinyl-1-oxy-3carboxylic acid; 2,2,3,3,5,5,6,6,-octamethyl-1,4-diazacyclohexyl-1,4dioxy; sodium nirosophenolate; copper compounds such as copper dimethyldithiocarbamate; copperdiethyldithiocabamate; copper dibutyldithiocarbamate; copper salicylate; methylene blue; iron; phenothiazine; 1,4-benzenediamine, N-(1,4-dimethylpentyl)-N'-phenyl; 1,4-benzenediamine,N-(1,3-dimethylbutyl)-N'-phenyl; isomers thereof; or mixture of two or more thereof.

Preferably, the used inhibitor is hydroquinone or a blend of N,N'-di-isopropyl-p-phenylenediamine with N-phenyl-N'-(1,3-dimethylbutyl)p-phenylenediamine, otherwise 4-Hydroxy-2,2,6,6-tetramethylpiperidine 1-oxyl, otherwise a blend of these inhibitors.

The inhibitor INHIB can be the same or different for each column. However, the inhibitor has to be mixed with a solvent which is different for each column. Indeed, for the first column 210, inhibitor is preferably diluted in methanol or in water. It is introduced in different points: at the first condenser 231 (inlet I4 on FIG. 2), at the lateral settler 223 (inlet I3 on FIG. 2) and in the upper part of the first column 210 (inlet I1 on FIG. 2). For the second column 250, it is better to prepare inhibitor with pure MMA. For that, pure MMA is extracted (not shown) from upper part of second column and mixed with inhibitor, and the mixture is then re-injected at the top of the upper part of the second column (inlet I2 on FIG. 2). The inhibitor is not introduced in the condenser 261 of the second column as for the first column, because pure MMA outlet must remain without any inhibitor. Each inhibitor inlet in the purification unit, has a flowrate control by individual rotameters (not shown on FIG. 2).

According to a variant, it is also possible to introduce in at least one reboiler of at least one of the columns, a small amount of poor air, in order to make the inhibitor more efficient.

Indeed some inhibitors like for example inhibitors of the hydroquinone type or of amine type, need a little quantity of oxygen to be more efficient and to prevent radical polymerization. However, MMA is also flammable in the presence of oxygen. That is why poor air is introduced, with a volumic ratio of oxygen comprised between 6% and 8%. This volumic ratio is a good compromise to avoid flammable area while increasing efficiency of inhibitor.

Concerning the distillation columns, random packing or structured packing may increase polymerization speed of MMA because polymers may cling to the packing and grow up. Moreover, in case of polymers formation such columns are not easy to clean. Therefore, both upper and lower parts of both distillation columns are preferably made of trays, or plates, respectively referenced 290, 214, 215, 254, 255 on FIG. 2. Different kinds of known trays can be used, like for example bubbled caps trays, plate with holes, both kinds with or without downcorners. Dual flow trays can also be used or other kinds of plates or trays. Such trays retain certain quantity of liquid, which flows downward the column, and let pass vapour through them upward the column.

Each column can have the same or different kind of trays between upper and lower part, and first and second column can have the same or different trays. The kinds of trays of each part of each column are chosen according to constraints, like flow rate of liquid and/or gas phase in the column for example.

Preferably, upper part and lower part of each distillation column have both between 4 and 30 trays or plates. This number of trays allows having an optimum separation of the components of the mixture to distil.

Preferably, all the parts of the purification unit 200, i.e all the parts of the distillation columns 210, 250, condensers systems 230, 260, lateral extraction system 220, reboilers 241, 271, pumps 239, 269 242, 272, etc. . . . are made of stainless steel. Such material is more resistant against corrosive products like methacrylic acid and acetic acid for example, which are present in the mixture to distil with molar ratios less than 10%. Moreover, stainless steel prevents pollution of pure MMA by metal oxide which may appear with other kinds of metal.

Each distillation column 210, 250 comprises at the top a safety valve 205, 206. In case of failure of either vacuum system 236, 266 or condenser system 230, 260, pressure inside the corresponding column may increase and become so high that the column may break. To avoid such breakage, the safety valve 205, 206 can discharge overpressure towards a vent network or directly to atmosphere.

The feeding flow rate of each distillation column 210, 250 is controlled by means of a flowrate analyzer, such as a flowmeter D1, D2 and a control valve 287, 288.

The temperature inside each column 210, 250 has to be controlled precisely. Thus, at least two temperature sensors T3, T4, T5, T6 are placed at least at the bottom and the top of each column 210, 250. At the bottom, the temperature sensor T3, T5 may be placed either at an upper tray of the lower part of the column or at the bottom, near the reboiler 241, 271. The bottom temperature is controlled by adjusting the flowrate of the steam in the reboiler 241, 271. The bottom temperature is therefore precisely controlled in order to check the maximum temperature and therefore to avoid MMA polymerization. The top temperature of both columns 210, 250, measured by temperature sensor T4, T5, is controlled by adjusting the reflux rate of the liquid phase recycled at the top of the columns and coming from the respective condensers systems 230, 260 and reflux drums 234, 264.

At least two pressure sensors P3, P4, P5, P6 are also placed at least at the bottom and the top of each column in order to control the pressure. The sensors are connected to alarm and safety valves (not shown), in case of problem. The pressure drop ΔP of each column 210, 250 is principally supervised because of flooding but it is also supervised because of clogging and fouling risks. Indeed, the trays of the columns may be clogged if the liquid phase is contaminated with formed polymers.

The purification unit that has been described presents a lot of advantages. First, it enables to produce very high quality of methyl methacrylate in a simple manner, with a reduced number of steps, namely only two successive distillations. The purity of the obtained MMA is higher than 99.90 wt % and more preferably higher than 99.96 wt %. Acidity in pure MMA is lower than 20 ppm and more preferably lower than 10 ppm. Water content is lower than 200 ppm and more preferably lower than 100 ppm. Total low boiling point impurities are lower than 500 ppm and more preferably lower than 400 ppm. Total high boiling point impurities are lower than 500 ppm and more preferably lower than 400 ppm. This high quality MMA is suitable to produce optical grade PMMA or to produce high quality PMMA or high quality methacrylates.

Another main advantage is the few losses of methyl methacrylate in low boiling point impurities or in high boiling point impurities. Indeed, during distillation, losses are lower than 0.5% and more preferably lower than 0.25%. The purification process yield is therefore very efficient.

Furthermore, the purification process is reliable because the MMA polymerization is well controlled.

Finally, the purification unit and associated process is suitable for purification of crude MMA obtained by various well-known processes.

The invention claimed is:

1. A methyl methacrylate purification unit (200) able to separate methyl methacrylate (MMA) from light and heavy impurities, said unit being characterized in that it comprises:
    a first distillation column (210) and a second distillation column (250) in series, each distillation column fed with a mixture to be distilled into their median parts, in order to divide each distillation column into upper (213, 253) and lower (212, 252) parts,
    wherein each upper (213; 253) and lower (212; 252) part of each distillation column (210, 250) comprises between 4 and 30 trays or plates (214, 215, 290; 254, 255), the first distillation column (210) being fed with a first mixture comprising a crude MMA comprising light and heavy impurities, and the second distillation column (250) being fed with a second mixture comprising a distilled liquid stream containing MMA, separated from light impurities, issued from the bottom of first distillation column (210), and the upper part (213) of the first distillation column (210) is connected to a lateral extraction system (220), able to minimize an MMA content in an obtained vapor of light impurities flowing upward said first distillation column (210),
    wherein the bottom of each distillation column (210, 250) is connected to a reboiler system (241; 271) that is able to re-inject a respective vaporized part of a first liquid phase and a second liquid phase, respectively into the respective lower parts (212, 252) of said distillation columns, while a part of each respective liquid phase flows towards a respective pump (242, 272), wherein the distilled liquid stream from the first reboiler system (241) comprises less than 200 ppm of water, less than 10 ppm of methanol and/or acetone and less than 500 ppm of total light impurities,
    wherein the lateral extraction system (220) comprises a feeding pipe (221) for adding cold water to a stream comprising light impurities and containing an MMA-water azeotropic mixture extracted from an extraction liquid outlet (216) located in the upper part (213) of first distillation column (210), a cooling device (222) for cooling the stream containing the azeotropic mixture and the cold water obtained from the extraction liquid outlet, wherein said cooling device is fed with cooling water having at a temperature between 20° C. and 34° C., and a settler (223) for obtaining a phase separation between an aqueous phase containing water and methanol, and an organic phase containing MMA and light impurities, said settler (223) being connected to an inlet (217) of the first distillation column (210) located below said extraction liquid outlet (216), in order to re-inject the organic phase containing MMA inside the upper part (213) of said first distillation column (210),
    wherein the top of each distillation column (210, 250) is connected to respective condenser systems (230, 260) for liquefying the obtained vapor of the first distillation column and an obtained vapor of the second distillation column, respectively, the condenser systems comprising reflux drums (234; 264) which recover respective obtained liquid streams from the respective condensers, and pumps (239, 269) which recycle parts of said obtained liquid streams into the respective upper parts (213, 253) of said distillation columns, wherein each condenser system (230, 260) comprises a first condenser (231; 261) being fed with cooling water at a temperature between 20° C. and 34° C. and a second condenser placed downstream of the first condenser and fed with chilling water at a temperature between 4° C. and 15° C., wherein each condenser system (230, 260) further comprises another condenser (235; 265) fed with liquid brine or glycol water at a temperature comprised between −20° C. and −5° C.,
    wherein said upper parts (213, 253) of each distillation column (210, 250) comprise respective inlets (I1, I2) for feeding an inhibitor (INHIB) able to prevent polymerization of MMA, wherein said settler (223) and said first condenser (231) of said first condenser system (230) each comprise inlets (I3, I4) for feeding the inhibitor (INHIB) able to prevent polymerization of MMA.

2. The methyl methacrylate purification unit according to claim 1, wherein the settler (223) further comprises an outlet (224) at its bottom through which the aqueous phase flows to be recycled towards a washing unit of crude methyl methacrylate (MMA).

3. The methyl methacrylate purification unit according to claim 1, wherein both distillation columns (210, 250) are connected to respective vacuum systems (236, 266) in order to have pressures at the bottoms of said distillation columns of between 66.66 mbar and 666.6 mbar.

4. The methyl methacrylate purification unit according to claim 3, wherein said pressure inside said second distillation column (250) is lower than said pressure inside said first distillation column (210).

5. The methyl methacrylate purification unit according to claim 1, wherein temperatures inside each distillation column are lower than 90° C.

6. The methyl methacrylate purification unit according to claim 1, wherein the inhibitor (INHIB) may be the same or different for each distillation column and is selected from the group consisting of: hydroquinone; 4-alcoxyphenol; hydroquinone monobenzylether; 1.2-dihydroxybenzene, 2-methoxyphenol; 2,5-dichlorohydroquinone; 2,5-di-ter-butylhydroquinone, 2-acethylhydroquinone; hydroquinone monobenzoate; 1,4-dimercaptobenzene, 1,2-dimercaptobenzene; 2,3,5-trimethylhydroquinone; 4-aminophenol, 2-aminophenol; 2-N,N-dimethylaminophenol; 2-mercaptophenol; 4-mercaptophenol; catechol; monobutylether; 4-ethylaminophenol; 2,3-dihydroxyaminophenone; pyrogallol; 1,2-dimethylether; 2-methylthiophenol; t-butyl catechol; di-ter-butylnitroxide; di-ter-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-ethanoyloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pirrolinyl-1-oxy-3 carboxylic acid; 2,2,3,3,5,5,6,6,-octamethyl-1,4-diazacyclohexyl-1,4dioxy; sodium nirosophenolate; copper compounds such as copper dimethyldithiocarbamate; copperdiethyldithiocabamate; copper dibutyldithiocarbamate; copper salicylate; methylene blue; iron; phenothiazine; 1,4-benzenediamine, N-(1,4-dimethylpentyl)-N'-phenyl; 1,4-benzenediamine,N-(1,3-dimethylbutyl)-N'-phenyl; isomers thereof; and a mixture of two or more thereof.

7. The methyl methacrylate purification unit according to claim 1, wherein said unit comprises a condenser system (260) downstream of the second distillation column (250) providing a pure MMA stream and a heat exchanger (267) fed with liquid brine or glycol water at a temperature comprised between −20° C. and −5° C. to chill the pure MMA at a temperature of 0° C.

8. The methyl methacrylate purification unit according to claim 1, wherein the top of each distillation column (210; 250) comprises a safety valve (205; 206) connected either to a vent network or to the atmosphere.

9. The methyl methacrylate purification unit according to claim 1, wherein all parts of the unit (200) are made of stainless steel.

10. The methyl methacrylate purification unit according to claim 3, wherein said unit comprises a plurality of temperature sensors (T1 to T6) placed at least at the bottom and at the top of each distillation column (210, 250), on the lateral extraction system (220) and on an exit from the heat exchanger (267) of a stream (268) of pure MMA, and a plurality of pressure sensors (P1 to P6) placed at least on a suction part of each vacuum system (236; 266) and at the bottom and at the top of each distillation column (210, 250).

11. A process for purifying crude methyl methacrylate (MMA) using the methyl methacrylate purification unit of claim 1, said crude MMA being pre-washed with water before the purification, said process comprises the following steps:
introducing the pre-washed crude MMA comprising light and heavy impurities in the median part of the first distillation column (210) in order to divide said first column into the lower (212) and the upper (213) parts, wherein at least 90% of the introduced MMA and the heavy impurities flow downwardly in said first distillation column (210) with the first liquid phase, and at least 98% of introduced light impurities flow upward with the obtained vapor, the first liquid phase being laterally extracted at the extraction liquid outlet located in the upper part of said first distillation column in order to be cooled and washed with the cold water and to obtain the phase separation between the aqueous phase containing water and methanol, and the organic phase containing MMA and light impurities which is recycled into said upper part (213) of said first distillation column (210), below said extraction liquid outlet; and
introducing the second mixture comprising the distilled liquid stream issued from the bottom of the first distillation column (210) into the median part of the second distillation column (250) in order to divide said second distillation column into the lower (252) and the upper (253) parts, wherein at least 98% of the introduced heavy impurities flow downwardly in said second distillation column (250) with the second liquid phase, while at least 90% of the introduced MMA flows upwardly with obtained vapor.

12. The process for purifying crude MMA according to claim 11, wherein the pressure at the bottom of each distillation column is comprised between 66.66 mbar and 666.6 mbar.

13. The process for purifying crude MMA according to claim 11, wherein said temperature inside each distillation column is lower than 90° C.

14. The process for purifying crude MMA according to claim 11, wherein the gas phase at the top of each column (210, 250) is partially liquefied with a condenser system (230, 260) and recycled at the top of said column.

15. The process for purifying crude MMA according to claim 11, wherein the liquid phase at the bottom of each column (210, 250) is partially vaporized and the obtained vaporized part is recycled into the lower parts of said respective distillation columns.

16. The process for purifying crude MMA according to claim 11, wherein a inhibitor (INHIB) preventing polymerization of MMA is introduced at least at the top of each column.

17. The process according to claim 16, wherein before being introduced in said first distillation column (210), said inhibitor (INHIB) is mixed with a solvent, which is chosen from water or methanol.

18. The process according to claim 16, wherein before being introduced in said second distillation column (250), said inhibitor (INHIB) is mixed with a solvent, which is pure MMA taken from the upper part (253) of said second distillation column.

19. The process according to claim 16, wherein said inhibitor (INHIB) is also introduced in the first condenser (231) of the first condenser system (230) connected to first distillation column (210), and in the settler (223) designed for the lateral extraction step.

20. The process according to claim 15, wherein poor air is introduced in at least one reboiler system (241; 271) of at least one distillation column, said poor air comprising a volumic ratio of oxygen between 6 and 8%, in order to improve efficiency of said inhibitor (INHIB).

21. The process according to claim 16, wherein said inhibitor may be the same or different for each distillation column and is selected from the group consisting of: hydroquinone; 4-alcoxyphenol; hydroquinone monobenzylether; 1.2-dihydroxybenzene, 2-methoxyphenol; 2,5-dichlorohydroquinone; 2,5-di-ter-butylhydroquinone, 2-acethylhydroquinone; hydroquinone monobenzoate; 1,4-dimercaptobenzene, 1,2-dimercaptobenzene; 2,3,5-trimethylhydroquinone; 4-aminophenol, 2-aminophenol; 2-N,N-dimethylaminophenol; 2-mercaptophenol; 4-mercaptophenol; catechol; monobutylether; 4-ethylaminophenol; 2,3-dihydroxyaminophenone; pyrogallol; 1,2-dimethylether; 2-methylthiophenol; t-butyl catechol; di-ter-butylnitroxide; di-ter-amylnitroxide; 2,2,6,6-tetramethyl-piperidinyloxy; 4-hydroxy-2,2,6,6-tetramethyl-piperidinyloxy; 4-oxo-2,2,6,6-tetramethyl-piperidinyloxy; 4-ethanoyloxy-2,2,6,6-tetramethyl-piperidinyloxy; 2,2,5,5-tetramethyl-pyrrolidinyloxy; 3-amino-2,2,5,5-tetramethyl-pyrrolidinyloxy; 2,2,5,5-tetramethyl-1-oxa-3-azacyclopentyl-3-oxy; 2,2,5,5-tetramethyl-3-pirrolinyl-1-oxy-3carboxylic acid; 2,2,3,3,5,5,6,6,-octamethyl-1,4-diazacyclohexyl-1,4dioxy; sodium nirosophenolate; copper compounds such as copper dimethyldithiocarbamate; copperdiethyldithiocabamate; copper dibutyldithiocarbamate; copper salicylate; methylene blue; iron; phenothiazine; 1,4-benzenediamine, N-(1,4-dimethylpentyl)-N'-phenyl; 1,4-benzenediamine,N-(1,3-dimethylbutyl)-N'-phenyl; isomers thereof; and a mixture of two or more thereof.

22. The process according to claim 20, wherein temperatures at the tops of each distillation column (210; 250) are controlled by adjusting respective reflux flowrates at the tops of the distillation columns and the temperatures at the bottoms of the distillation columns (210; 250) are controlled by adjusting flowrates of steam in the reboiler systems (241; 271) designed for the vaporization of the first and second liquid phases.

23. The process according to claim 11, wherein pressures at the tops of each distillation column are controlled to prevent polymerization of MMA and differential pressures between the respective tops and the bottoms of each distillation column are supervised so as to prevent flooding, clogging and fouling of said distillation columns.

24. The process according to claim 11, wherein the second liquid phase comprising heavy impurities exits the bottom of second distillation column (250) and is pumped towards an esterification unit of an MMA production plant.

* * * * *